United States Patent [19]

Andersen et al.

[11] Patent Number: 4,761,268

[45] Date of Patent: Aug. 2, 1988

[54] LIQUID HANDLING

[75] Inventors: Marlo R. Andersen, Veradale; Thomas O. Tiffany, Spokane, both of Wash.; Mario J. Gangitano, Anaheim, Calif.

[73] Assignee: Fisher Scientific Company, Pittsburgh, Pa.

[21] Appl. No.: 599,509

[22] Filed: Apr. 12, 1984

[51] Int. Cl.[4] .................... G01N 21/07; G01N 35/06
[52] U.S. Cl. ...................................... 422/72; 422/63; 422/100; 422/102
[58] Field of Search .................. 422/64, 63, 67, 72, 422/100, 102; 141/130, 98, 83, 94, 392, 1; 436/47, 54

[56] References Cited

U.S. PATENT DOCUMENTS

| | | | |
|---|---|---|---|
| 3,081,158 | 3/1963 | Winter | 141/130 |
| 3,801,283 | 4/1974 | Shapiro et al. | 422/72 |
| 3,873,217 | 3/1975 | Anderson et al. | 422/72 |
| 4,170,625 | 10/1979 | Welch | 422/64 |
| 4,287,155 | 9/1981 | Tersteeg et al. | 422/100 |
| 4,311,667 | 1/1982 | Gocho | 141/130 |
| 4,344,768 | 8/1982 | Parker et al. | 422/100 |
| 4,456,037 | 6/1984 | Gocho | 422/100 |

FOREIGN PATENT DOCUMENTS

2081897 2/1982 United Kingdom ................. 422/64

Primary Examiner—Michael S. Marcus

[57] ABSTRACT

A liquid handling system that is particularly useful in a clinical analysis system includes a cuvette loading station for receiving a centrifugal analyzer rotor with two compartment cuvettes. Fixedly mounted on transfer structure are two spaced apart liquid handling probes such that the two probes may be simultaneously inserted into the two compartments of an analysis cuvette. A sample station has a sample container support mechanism, and means for indexing the support mechanism past the sample station for sequentially positioning successive sample containers at the sample station. An auxiliary station that is spaced from the sample station a distance corresponding to the spacing of the two probes includes a support mechanism for supporting a plurality of auxiliary containers and a drive mechanism for selectively positioning auxiliary containers at the auxiliary station. A first drive provides relative movement between the transfer structure and the loading sample and auxiliary stations; a second drive is adapted to concurrently insert the tips of the two liquid handling probes into containers at the loading, sample or auxiliary stations. First and second liquid metering means are coupled to the probes by storage chamber structure so that each metering means controls the flow of a liquid into and out of its storage chamber through its probe; and control means operate the drive mechanisms and the liquid metering means in coordinated manner to transfer sample and reagent materials from sample and auxiliary containers at the sample and auxiliary stations to an analysis cuvette at the loading station. The system provides coordinated automatic pipetting and transfer of sample, diluent and reagent liquids in rapid, efficient and precise manner.

18 Claims, 6 Drawing Sheets

LIQUID HANDLING

This invention relates to analysis systems and more particularly to liquid handling apparatus for delivering liquids in predetermined proportions to analysis chambers for measurement or other testing.

In automated chemical analysis systems, raw or dilute sample is frequently mixed with one or more reactants for analysis. For example, in a clinical chemistry analysis system, minute quantities of a serum sample are mixed with various quantities of different reactants to provide chemical reactions that enable measurement of particular constituents of the serum sample. The sample liquid to be analyzed is frequently diluted to provide a sample volume which can be more easily processed.

Clinical analyzers of the centrifugal type are useful in performing a variety of analyses, including kinetic and endpoint analyses, by such techniques as absorption, light scattering and/or fluorescence. In general such analyzers utilize a multicuvette rotor assembly which has a centrifugal array of spaced elongated radially extending curvettes, each of which has an inner chamber for initially holding a first reactant which frequently is a sample of blood or other biological fluid, and an outer chamber for initially holding one or more different reactants. The two chambers are separated by divider structure, and reactants transferred by centrifugal force to an analysis region at the outer end of the cuvette for mixing and reaction and subsequent analysis. The cuvettes of such rotor assemblies typically are loaded successively with automated loading equipment, small quantities of sample (2–20 microliters) typically being loaded into the inner chambers and reactants in quantities of up to 200 microliters being loaded into the outer chambers. The loaded rotor assembly is then transferred to an analyzer for analysis by methods such as photometric, light scattering, and/or fluorescence. In a typical analysis sequence, the rotor assembly is first spun at 100 rpm, then accelerated to about 4000 rpm for about one second for transferring the reactants from the inner chamber, then braked for mixing the sample and reactant, and then brought up to a speed of about 1000 rpm for analysis. Accurate measurement of sample and reactant volumes is essential, as well as providing the required volumes of sample and reactants to each cuvette in precise proportion.

In accordance with one aspect of the invention, there is provided a liquid handling system that is particularly useful in a clinical analysis system and includes a cuvette loading station for receiving an analysis cuvette that has two compartments. Fixedly mounted on transfer structure are two spaced apart, liquid handling probes such that the two probes may be simultaneously inserted into an analysis cuvette. A sample station has a sample container support mechanism, and means for indexing the support mechanism past the sample station for sequentially positioning successive sample containers at the sample station. An auxiliary station that is spaced from the sample station a distance corresponding to the spacing of the two probes includes a support mechanism for supporting a plurality of auxiliary containers and a drive mechanism for selectively positioning auxiliary containers at the auxiliary station. A first drive provides relative movement between the transfer structure and the loading sample and auxiliary stations; a second drive is adapted to concurrently insert the tips of the two liquid handling probes into containers at the loading, sample or auxiliary stations. First and second liquid metering means is coupled to the probes by storage chamber structure so that each metering means controls the flow of a liquid into and out of its storage chamber through its probe; and control means operates the drive mechanisms and the liquid metering means in coordinated manner to transfer sample and reagent materials from sample and auxiliary containers at the sample and auxiliary stations to an analysis cuvette at the loading station. The system provides coordinated automatic pipetting and transfer of sample, diluent and reagent liquids in rapid, efficient and precise manner.

In preferred embodiments, the sample container and auxiliary container support mechanisms are coaxial circular arrays that support the sample and auxiliary containers. Separate drives are provided for the independent positioning of containers at the auxiliary and sample stations respectively. In a dilution mode, a circular array of auxiliary containers is coupled for indexing with the circular array of sample containers. A secondary set of auxiliary (reagent) containers may be mounted for driving independently of the sample containers or may be substituted by the sample containers.

In accordance with another aspect, there is provided an apparatus for transferring precise quantities of liquid materials to analysis cuvettes that includes a cuvette loading station for receiving an analysis cuvette, transfer structure having cantilever arm structure with a liquid handling probe fixedly mounted at one end thereof, storage chamber structure connected to the probe, and liquid metering means connected to the storage chamber structure that controls flow of liquid into and out of the storage chamber through the probe. A sample station has a sample container support, and sample container drive mechanism for moving the sample container support past the sample station to sequentially position successive sample containers at the sample station. The system also includes a first drive mechanism for providing translational movement between the cantilever arm structure and the loading and sample stations, a second drive mechanism for moving the tip of the liquid handling probe in a direction generally perpendicular to the translational movement of the cantilever arm structure to insert the probe into and withdraw the probe from containers at the loading and sample stations, and control means for operating the drive mechanisms and the liquid metering means to draw a precise quantity of sample from a sample container at the sample station into the probe and deliver the precise quantity to an analysis cuvette at the loading station.

In a particular embodiment, the first drive includes a lead screw for translating the cantilever arm structure between the loading and sample stations and the second drive includes cam structure disposed for rotation about an axis parallel to the lead screw for pivoting the cantilever arm structure. The cantilever arm structure includes releasable latch structure arranged to disconnect the cantilever arm from the second drive in response to a force of less than twelve ounces resisting the insertion movement of said probe.

The cuvette loading station is adapted to receive a centrifugal analyzer rotor that has a plurality of analysis cuvettes arranged in annular array, each analysis cuvette having two compartments with corresponding spaced loading ports, and the two probes are spaced corresponding to the spacing of the analysis cuvette loading ports. The sample and auxiliary container supports position a plurality of containers in coaxial annular arrays. The sample container support includes tray structure with an annular array of sockets in which sample containers are removably received, and the tray may be coupled to the auxiliary container support for rotation by the auxiliary container support drive mechanism in synchronism with the auxiliary container support. The auxiliary container drive mechanism also includes means for rotating the auxiliary container support independently of the sample container drive mechanism so that sample and auxiliary containers may be selectively and independently positioned at the sample and auxiliary stations respectively.

A reagent container tray structure is removable and interchangeable with sample container tray structure so that the reagent container tray structure may be substituted for the sample container tray structure and vice versa.

The system employs auxiliary containers of sector shaped configuration that have a generally vertical curved outer wall, generally vertical side walls that are disposed at an angle to one another, a generally horizontal top wall with a first port through which a probe carried by the transfer structure may be inserted, and a generally horizontal bottom wall that has a well portion below and aligned with the first port in the top wall. A dry well channel in the container that is aligned with a second port in the top wall allows one of the probes to be inserted concurrently with the insertion of the other probe through the first port.

The system also includes a wash station that has two wells spaced to receive the two probes carried by the transfer structure. Each well has a width dimension slightly larger than the outside dimension of the probe so that liquid discharged from the probe while the probe is in the well flows upwardly along the outer surface of the probe in cleaning action. A peripheral wall upstanding from and extending around the tops of the two wells defines a containment chamber and a drain port in the base of the containment chamber transfers excess liquid to waste. A valve arrangement selectively connects each syringe type metering means to a diluent supply and to its corresponding storage chamber. Each syringe, when connected to the diluent supply, draws diluent into the syringe chamber and when connected to its storage chamber, controls flow of liquid into and out of that storage chamber through its probe.

The liquid handling system has a numerical keypad, a control keypad, and an alpha-numeric display which displays stored loading parameters, user selected input parameters, operator prompts, and diagnostic/error messages. The user can select starting sample position, number of samples, reagent/sample volumes and similar loading parameters. Stored chemistry programs, operator defined chemistry programs, and operator entered specific sample and reagent volume programs are available. Selected sample and reagent volume settings are displayed, together with the reference cuvette identification, position of the first sample, number of samples, and second reagent volume (if selected). The system will load a twenty-cuvette rotor, starting at a designated reference cuvette position and sequentially loading up to twenty cuvettes with sample and a single reagent in three minutes. The loading time for twenty cuvettes with sample and two reagents is four minutes. Sample volumes from two to ninety-nine microliters and reagent volumes from five to two-hundred fifty microliters may be selected.

Other features and advantages will be seen as the following description of a particular embodiment progresses, in conjunction with the drawings, in which.

DESCRIPTION OF PARTICULAR EMBODIMENT

Figure 1:
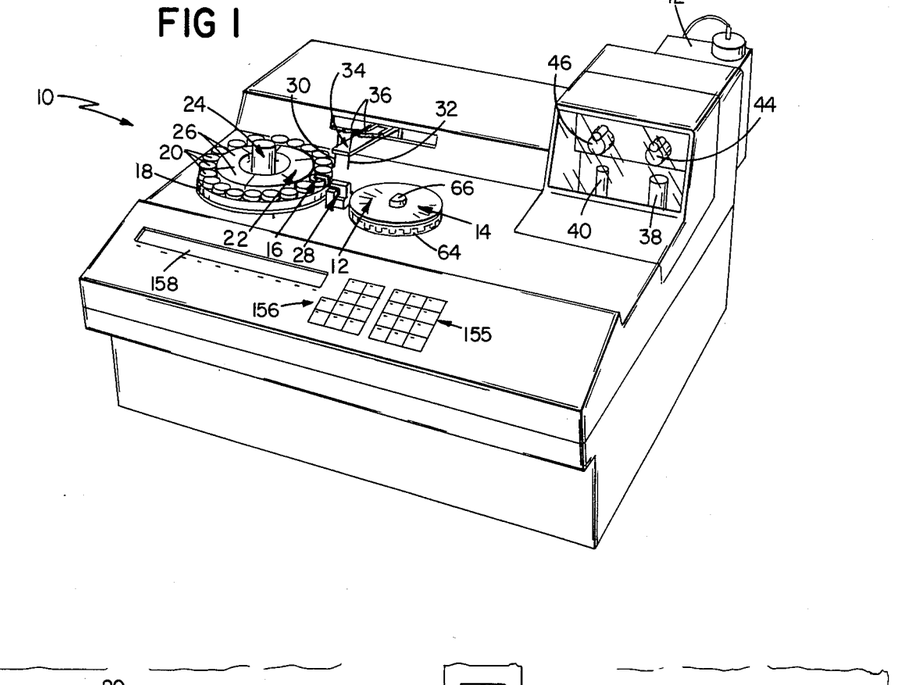
FIG. 1 is a perspective view of liquid handling apparatus in accordance with the invention.
Figure 13:
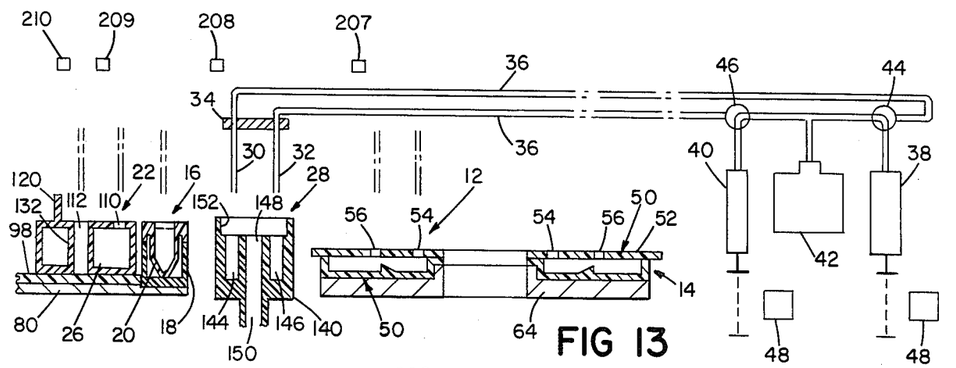
FIG. 13 is a diagrammatic view of components of the liquid handling system similar to FIG. 3.

The liquid handling apparatus 10 shown in FIG. 1 has a cuvette loading station 12 for loading a twenty-cuvette analysis rotor 14 of the type shown in Tiffany U.S. Pat. Nos. 4,226,531 or Stein 4,373,812; a sample station 16 associated with a sample vessel transport ring 18 that has capacity for twenty sample cups 20 disposed in circular array; a reagent station 22 associated with a reagent container transport table 24 that has capacity for for six reagent boats 26 arranged in circular array; and a wash station 28 disposed between cuvette loading station 12 and sample station 16. Transfer pipettes 30, 32 are mounted on transport arm assembly 34 and are connected via storage chamber tubing 36 to metering pumps 38, 40 respectively. Diluent supply (distilled water) 42 is connected to metering pumps 38, 40 via three-way valves 44, 46 (FIGS. 1 and 13). Metering pump 38 has a capacity of two-hundred fifty microliters and metering pump 40 has a capacity of one-hundred microliters, each metering pump including a piston that is driven by a precision stepper motor 48 (FIG. 13).

Figure 2:
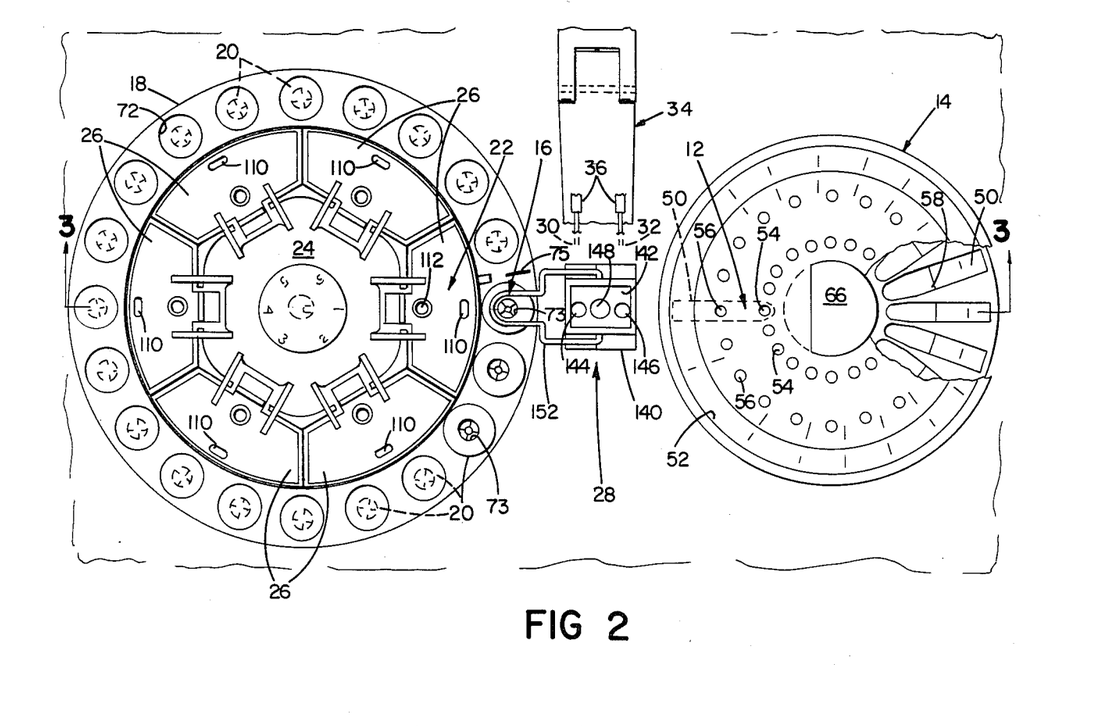
FIG. 2 is a top plan view (with portions broken away) showing details of reagent, sample, wash and loading stations of the liquid handling apparatus shown in FIG. 1.
Figure 3:
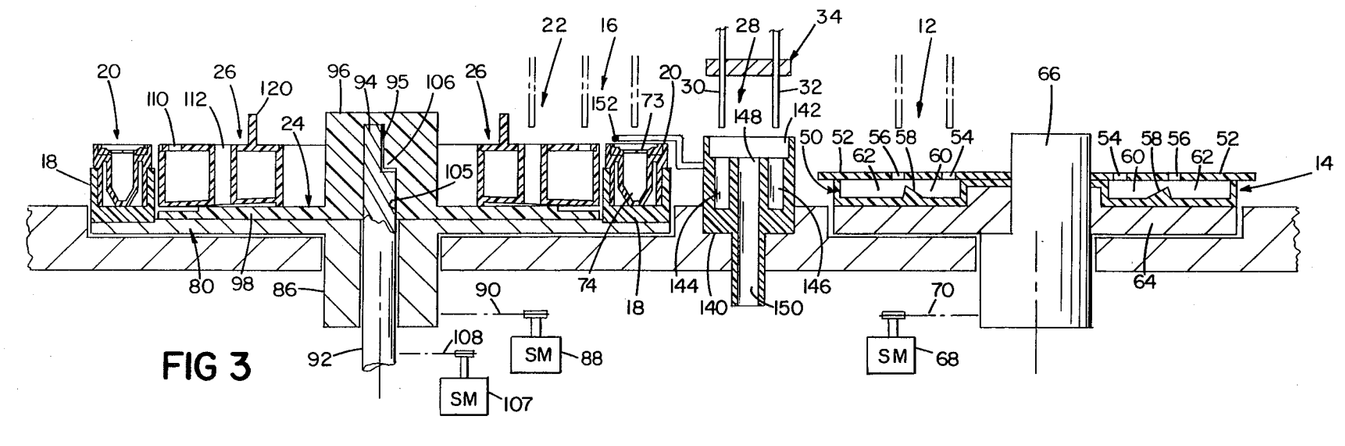
FIG. 3 is a view, partially in section and partially diagrammatic, taken along the line 3—3 of FIG. 2.

Further details of the cuvette loading, sample, reagent and wash stations may be seen with reference to FIGS. 2 and 3. As shown in FIGS. 2 and 3 and the diagrams of FIGS. 13-17, the cuvette loading, sample, reagent and wash stations are disposed along a straight line path, and the tips of transfer pipettes 30, 32 are disposed on and are arranged to move along that straight line path.

Analysis rotor 14 is of the type shown in the above mentioned Tiffany and Stein et al. patents, and has a diameter of about ten centimeters, an overall height of about ⅜ centimeter, and defines a circumferential array of twenty individual cuvettes 50 with an optical window region 52 adjacent its periphery. Each cuvette 50 has two loading ports 54, 56 and internal barrier structure 58 which separates inner and outer chambers 60, 62 of the cuvette. Rotor 14 is received on rotor transport table 64 which has upwardly projecting drive shaft 66 that is coupled to stepper motor 68 by drive belt 70 for indexing cuvettes 50 sequentially past cuvette loading station 12.

Figure 4:
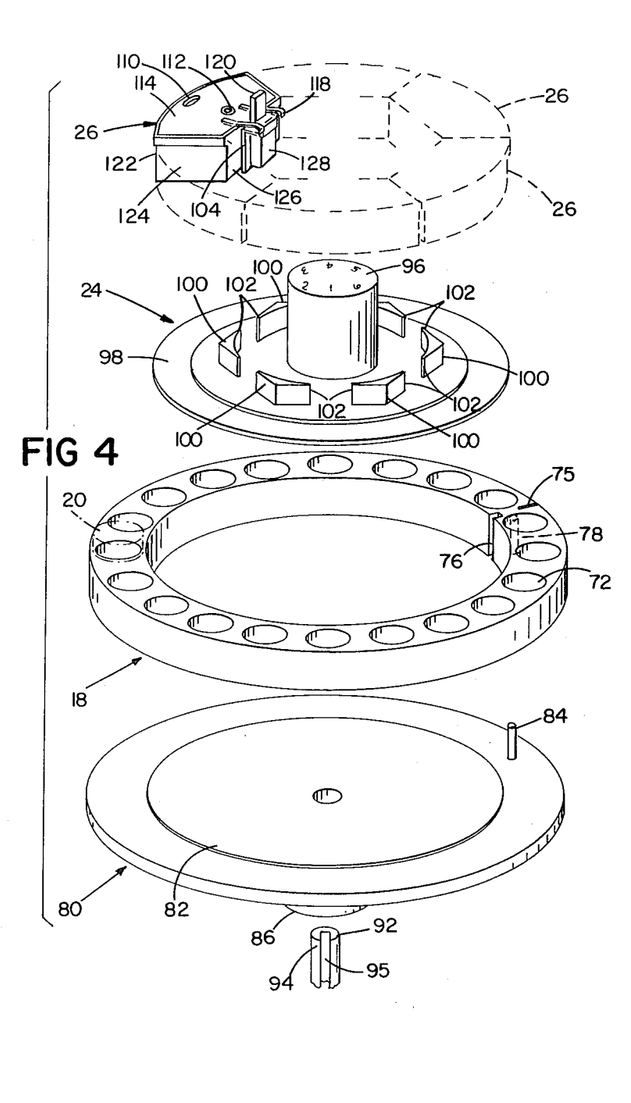
FIG. 4 is an exploded perspective view of components at the reagent and sample stations.

Details of sample transport ring 18 may be seen with reference to FIGS. 2, 3 and 4. Sample ring 18 has an inner peripheral dimension of about eleven centimeters, an outer peripheral dimension of about fourteen centimeters, a height of about one centimeter, and has a series of twenty sockets 72 which receive sample cups 20. Each sample cup 20 has a capacity of one quarter milliliter volume, a cover 73 to reduce evaporation, and a conical base 74 to minimize dead volume in the sample cup. Transport ring 18 also carries an index mark 75 which is aligned with keyway 76 in its inner periphery and has a drive socket 78 in its lower surface. Transport ring 18 is seated on drive table 80 (FIG. 4) which has a cylindrical ring aligning ridge 82 and carries an upwardly projecting drive pin 84 that is inserted in drive socket 78. The depending hub 86 of table 80 is coupled to stepper motor 88 by drive belt 90 for indexing the sample ring 18 past sample station 16.

Figure 5:
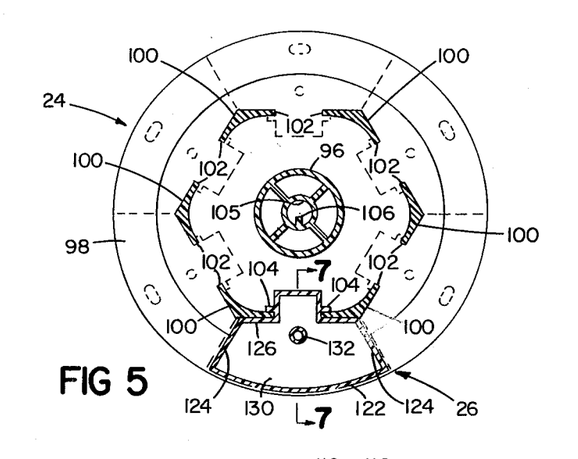
FIG. 5 is a plan view in section showing details of the reagent container transport tray.

Extending through table hub 86 is drive shaft 92 which has drive portion 94 at its upper end in which a keyway 95 is formed. The hub 96 of reagent container support table 24 is received in driving engagement on drive shaft portion 94. Table 24 has a radially extending support plate 98 and formed on plate 98 are a series of six upstanding male coupling elements 100, the edges 102 of which are received in female coupling slots defined by cooperating coupling flange portions 104 of reagent containers 26 as indicated in FIG. 5. Cylindrical socket 105 formed within hub 96 has a key 106 which is received in slot 95 of drive shaft 92 so that table 24 may be indexed by drive motor 107 via drive belt 108.

Figures 6, 7, 8:
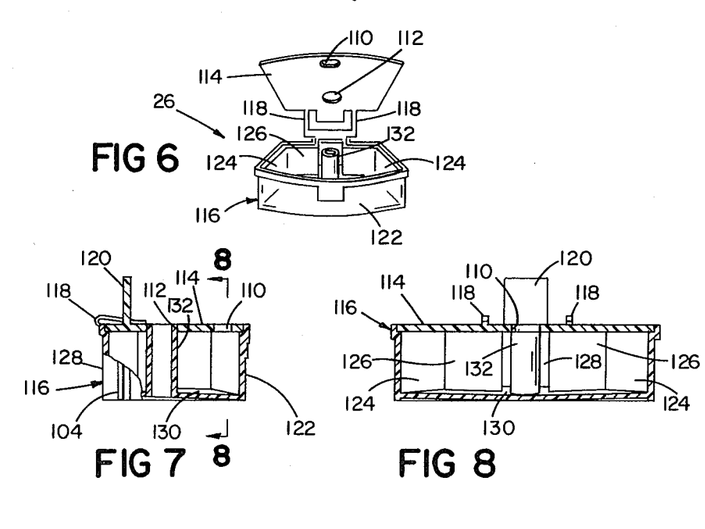
FIG. 6 is a perspective view of a reagent container employed in the reagent supply system shown in FIGS. 4 and 5.
FIG. 7 is a sectional view through a reagent container taken along the line 7—7 of FIG. 5.
FIG. 8 is a sectional view through a reagent container taken along the line 8—8 of FIG. 7.
Figure 9:
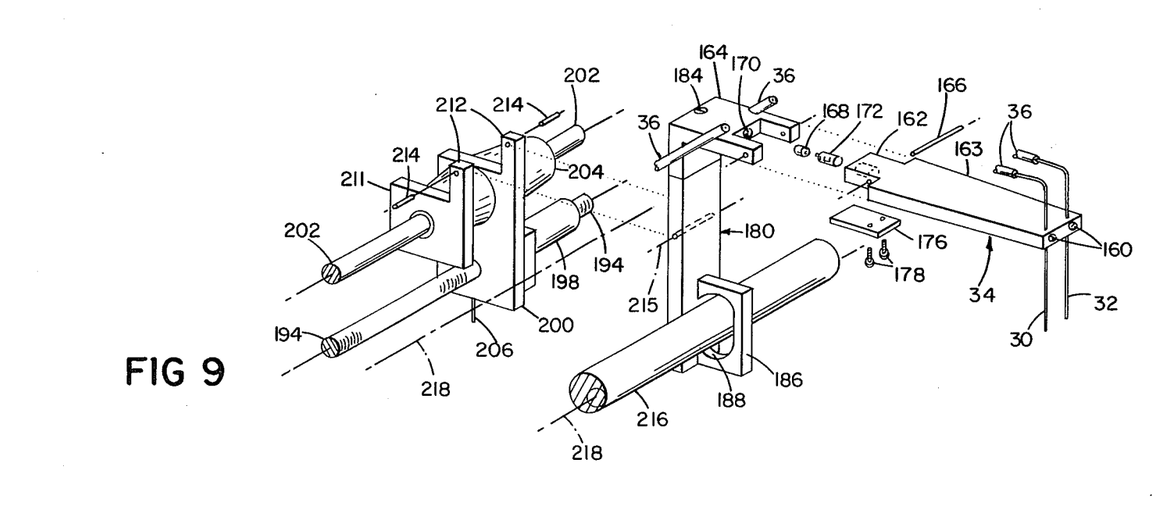
FIG. 9 is an exploded perspective view of components of the pipette probe transport mechanism employed in the transfer apparatus of FIG. 1.
Figure 10:
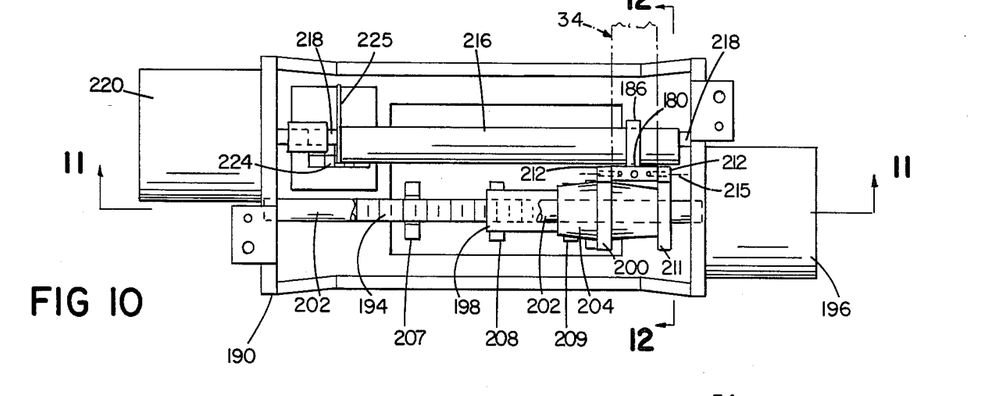
FIG. 10 is a top plan view of the pipette transport arm drive mechanism.
Figure 11:
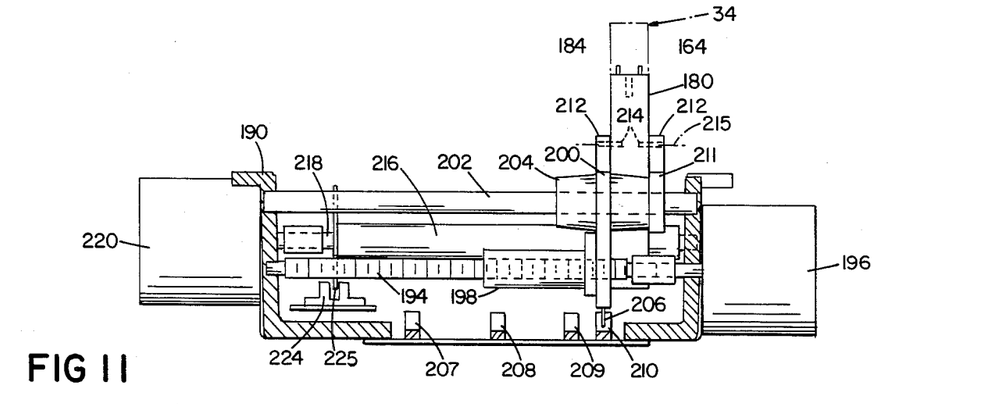
FIG. 11 is a sectional view taken along the line 11—11 of FIG. 10.

Reagent table 24 has a diameter of about eleven centimeters with central hub handle 96 having a height of about 2½ centimeters and carries an array of six sector shaped molded reagent containers 26 each of eight milliliter volume. Each container 26 has ports 110, 112 in its cover 114 that is attached to body 116 by two straps 118. Port 110 is about three millimeters wide and about six millimeters long and port 112 has a diameter of about six millimeters. A handle 120 projects upwardly from cover 114. Body 116 has curved front wall 122 (of about 5.5 centimeter radius), sidewalls 124 that are disposed at an angle of 60° to one another and rear wall 126. Rearwardly projecting bulge 128 (FIG. 4) carries flanges 104 that are spaced from the surface of wall 126 and receive the ends 102 of coupling elements 100 as indicated in FIG. 5 to releasably secure containers 26 on table 24. The base 130 of container 26 (as shown in FIGS. 7 and 8) is about one millimeter thick and has a slope of about three degrees from the rear and side walls 126, 124 to a point directly below port 110, so that the floor of container 26 is essentially conical with a well at the apex below port 110. Upstanding from base 130 is tubular dry well 132 that is open at the bottom and extends through the floor 130. Port 112 receives the top of dry well post 132 when cover 114 is closed so that the top of post 132 is essentially flush when the upper surface of cover 114 when that cover is closed.

With reference again to FIGS. 2 and 3, wash station 28 has a body 140 with a recess 142 of about one-half centimeter depth. Formed in recess 142 are two cylindrical wells 144, 146 (of 1.5 centimeter depth and 3.5 millimeter diameter) for receiving the tips of pipettes 30, 32 at the wash station and a drain port 148 that communicates via passage 150 to waste. Secured to and extending laterally from waste station member 140 is a sample cup hold down arm 152 which extends over sample station 16 (as indicated in FIGS. 2 and 3) and defines a port (as shown in FIG. 2) through which a probe tip moves. Arm 152 restrains possible upward movement of the sample cup 20 at the sample station 16 due to engagement of the probe with the evaporation cover 73 during withdrawal of the pipette 32.

With reference again to FIG. 1, the liquid handling apparatus 10 has a numerical keypad 155, a control keypad 156, and a forty character vacuum fluorescent alpha-numeric display 158 which displays stored loading parameters, user selected input parameters, operator prompts, and diagnostic/error messages. The user can select starting sample position, number of samples, reagent/sample volumes and similar loading parameters. Stored chemistry programs, operator defined chemistry programs, and operator entered specific sample and reagent volume programs are available. Selected sample and reagent volume settings are displayed, together with the reference cuvette identification, position of the first sample, number of samples, and second reagent volume (if selected). The system will load a twenty-cuvette rotor starting at a designated reference cuvette position and sequentially loading cuvettes 50 through the designated number of samples. Stored loading parameters for single reagent and two reagent chemistries are selected by keyboard entry—sample volumes from two to ninety-nine microliters and reagent volumes from five to two-hundred fifty microliters may be selected in a single reagent mode or a combined volume of sample and reagent in a two reagent mode, the minimum total volume dispensed into a cuvette 50 being one-hundred and fifty microliters.

Figure 12:
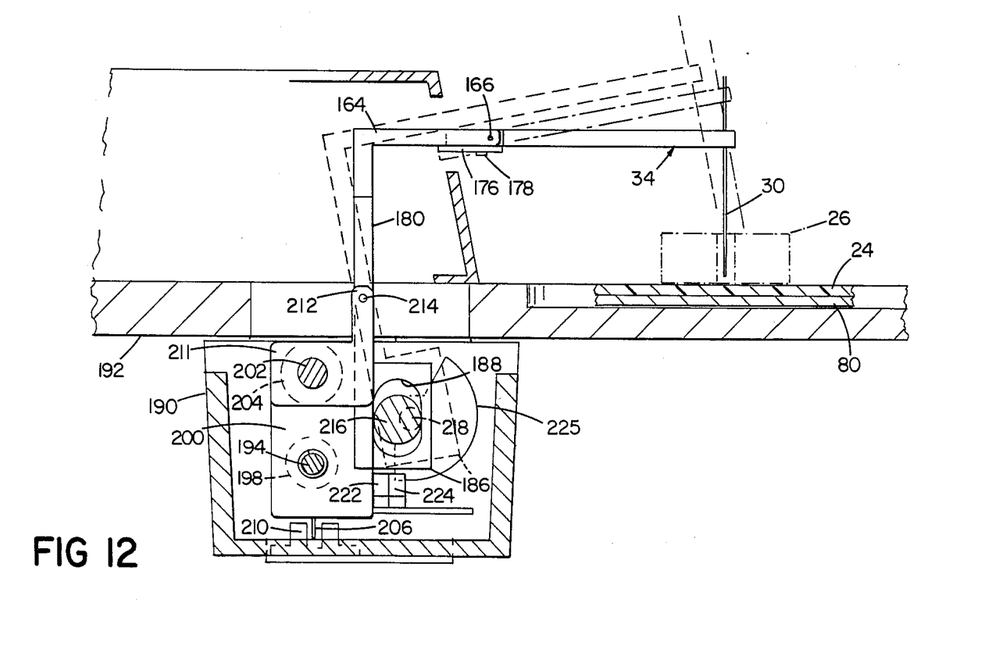
FIG. 12 is a sectional view taken along the line 12—12 of FIG. 10.

Further details of the pipette transport assembly 34 may be seen with reference to FIGS. 9-12. That pipette arm has a length of about eleven centimeters and carries at its forward end two pipette tubes 30, 32, with their tips fixed in alignment by set screws 160. Assembly 34 includes forward member 162 that is pivotally secured to rear member 164 by pivot shaft 166. A spring biased plunger unit 168 is received in socket 170 of rear member 164 and a cooperating threaded shaft 172 (that permits release force adjustment) is received in the rear end portion of the forward member 162. Limit plate 176 is secured by bolts 178 to the underside of member portion 162 and limits the downward pivoting movement of member 162 to a position aligned with member 164 (as shown in FIG. 12) in which position ball plunger unit 168 and shaft 172 are in latching engagement. The latch force is adjustable (by rotation of shaft 172) over a range of about three—twelve ounces at the pipette tips. When the selected force is exceeded, the latch releases and member 162 freely pivots upward (as indicated in chain line in FIG. 12), thus avoiding damage should there be an obstruction or the pipette tips be blocked from moving down to their lower position as indicated in full line in FIG. 12. Assembly 34 is mounted on arm 180 for pivoting movement about axis 215 on a transport arm drive mechanism, member 164 being secured to arm 180 by bolt 184 and dowel pins. Arm 180 carries cam follower member 186 that has an aperture 188 with opposed parallel cam follower surfaces.

Further details of the drive mechanism for the pipette transport assembly 34 may be seen with reference to FIGS. 9-12. That drive mechanism includes a cast aluminum housing 190 which is arranged for direct mounting on support frame 192 and which carries a one inch pitch lead screw 194 that is coupled to 1.8° stepping motor 196. Disposed on lead screw 194 is drive nut 198 to which is secured arm support 200. A ⅜ inch diameter stainless steel shaft 202 receives bushing assembly 204 that is attached to support 200 and provides support and guidance for the horizontal motion of that arm support. Pin 206 depending from support 200 cooperates with four optical sensors 207-210 which are located at positions corresponding to the cuvette loading station 12, wash station 28, sample station 16 and reagent station 22 respectively.

Support 200 and plate 211 attached to bushing 204 include spaced upstanding arms 212 that receive pivot pins 214 that support arm 180 and define pivot axis 215. Cam follower aperture 188 receives and cooperates with ⅜ inch diameter Nylatron cam shaft 216 that has stubs 218 so that shaft 216 has a ⅜ inch throw. Cam shaft 216 is directly coupled to 1.8° stepping motor 220 that rotates 165° to produce eleven degrees of angular lift of transport arm 34 (about 2.3 centimeters of vertical motion at the tips of pipettes 30, 32). As may be seen with reference to FIGS. 9-12, lead screw 194, guide shaft 102, and cam shaft 216 are disposed parallel to one another an parallel to the straight line path defined by the tips of pipette probes 30 and 32.

A vertical position indicator assembly has two masked optical switches 222, 224 which are operated by vertical disc 225 that is secured to and rotates with cam shaft 216. When the transport arm assembly 34 is in the down position, sensor 222 is on; when the arm 34 is in the up position, sensor 224 is on; and when the arm 34 is in an intermediate position, both sensors are off. Stops fixed to the casting 190 prevent the cam 216 from rotating beyond defined limits.

With reference to FIG. 13, in horizontal motion along the strighht line path, starting from the home position (over wash station 28—sensor 208) two-hundred sixty-six steps of motor 196 (0.005 inch per step) position the arm assembly 34 with pipette 32 at sample station 16 and pipette 30 at reagent station 22 (sensor 209). Rotation of motor 196 three-hundred ten steps in the opposite direction moves the transport assembly 34 from the wash station 28 to the loading station 12 (sensor 207). Rotation of motor 220 ninety-two steps moves the cam shaft 216 165° to pivot the arm assembly 34 over its eleven degree range, from the lower solid line position to the upper dotted line position as indicated in FIG. 12.

Further aspects of the loading system may be seen with reference to the simplified diagrams of FIGS. 13-17 which depict a sequence of operative positions of the dual probe assembly 34. Pipette tubes 30, 32 are physically attached to transport arm 34 and hydraulically connected to metering pumps 38, 40 respectively through tubes 36 (which function as storage chambers) and valves 44, 46 respectively. Each positive displacement metering device 38, 40 is of similar design and includes a cylindrical tube in which a piston is disposed. The system controller drives the metering motors 48 to move the pistons in microliter steps to load and dispense from the pipettes 30, 32. With the valves 44, 46 in a first position, each metering device draws diluent (usually reagent grade distilled water) from diluent reservoir 42.

Initially, the metering pumps 38, 40 and the connecting tubes 36 are filled with bubble-free diluent 226. To fill the tubes 36, the system places the valves 44, 46 in their first positions and the syringe motors 48 draw diluent from reservoir 42 into the metering chambers 38, 40. When the valves 44, 46 are shifted to their second position (connecting chambers 38, 40 to tube chambers 36), the pump motors 48 drive the pistons to dispense diluent from the cylinders 38, 40 through the storage chamber tubes 36 to the pipettes 30, 32.

Figure 14:
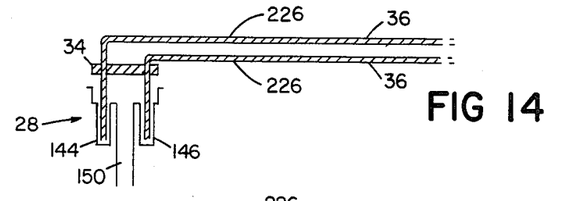
FIGS. 14–17 is a series of diagrammatic views showing aspects of operation of the liquid handling system.
Figure 15:
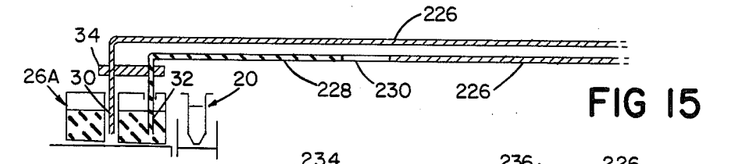

When the operator presses the wash key on the control panel 156, transport arm 34 is moved by motor 196 to the wash station 28 (FIG. 14). While arm 34 is moving to wash station 28, the syringes 38, 40 are completely filled from diluent reservoir 42. The three-way valves 44, 46 are then switched to tubs 36. When sensor 208 verifies the positioning of transport arm at wash station 28, a control interlock is released and motor 220 is energized to lower the pipette tips into wash bath chambers 144, 146. Metering pump motors 48 then empty the syringes of diluent liquid, air and air bubbles are flowed from the tips of tubes 30 and 32 into wash bath chambers 144, 146 and the discharged liquid flows up out of each well (cleaning the outer surfaces of the pipettes) and overflows from the probe chambers for discharge through passage 150 to waste. For a complete wash cycle, this sequence is repeated twenty times and the syringes 38, 40 are emptied before the tips of pipettes 30, 32 are raised above wash bath 28. In this condition, storage tubes 36 and pipette tips 30, 32 are filled with diluent 226 as indicated in FIG. 14. After arm 38 is raised, pumps 38, 40 may draw diluent 226 back from the pipette tips.

During the wash cycle, the sample table 80 and the reagent table 98 are indexed to position specified sample and reagent containers 20 and 26 at sample station 16 and reagent station 22 respectively. After the wash cycle is completed, transport arm 34 is lifted by cam 216 driven by motor 220, and moved by motor 196 to the sample position (sensor 209) if a single reagent is to be used, or to the reagent position (sensor 210) if the analysis is to employ two reagents.

Figure 16:
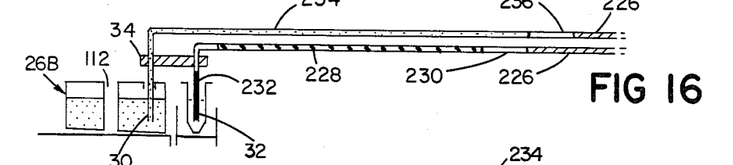

When the analysis employs two reagents, reagent table 98 is indexed by motor 112 to the specified reagent container position; the pipette tips are lowered into reagent container 26A (FIG. 15), reagent pipette 30 passing through the dry well port 112 and sample pipette 32 passing through container port 110. Metering syringe 40 then draws into pipette 32 and its associated storage chamber 36 the specified volume 228 of first reagent spaced from diluent 226 by air slug 230; transport arm 34 is then lifted and moves to the wash station 28 (FIG. 14) for a dip to remove residue on the outsides of the tips of pipettes 30, 32; and then the transport arm 34 moves to the sample station (sensor 209) and as indicated in FIG. 16 the pipette tips are lowered into the sample cup 20 and a different reagent boat 26B. Syringes 38 and 40 then draw up the specified volumes 232, 234 of sample and second reagent. As indicated in FIG. 16, pipette 32 contains the specified volume 232 of sample and the specified volume 228 of the first reagent spaced from diluent 226 by air bubble 230; and pipette 30 contains a specified volume 234 of the second reagent spaced from diluent 226 by air bubble 236. In cases of analyses that use a single reagent, the FIG. 15 step is omitted and arm assembly moves directly from wash station 28 to sample station 16. In all cases, the user has the option of drawing or omitting an air-bubble separator between sample, reagents and diluent.

Figure 17:
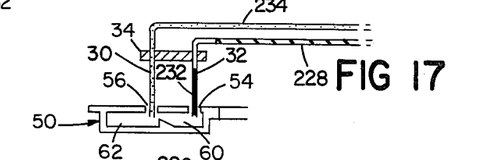

After the storage chambers 36 have been loaded with sample and reagent(s), the system controller moves the pipette arm 34 to the wash station 28 (sensor 208) where the pipettes 30, 32 are dipped by motor 220 to remove residue on the outside of the tips. The transport arm 34 is then raised by motor 220 and moved laterally by motor 196 to the loader station 12 (sensor 207) where the tips are lowered through the loading ports 54, 56 of the rotor cuvette 50 (as indicated in FIG. 17) and the syringe motors 48 are energized to dispense the pipetted volumes 228, 232 and 234 into the respective chambers 60, 62 of the cuvette. Since the tubing storage chamber 36 for each pipette is quite long and the volumes of sample and reagent quite small, neither sample nor reagent approaches the syringes 38, 40 or the valves 44, 46 to contaminate them.

After loading cuvette 50 (FIG. 17), the system control raises the pipettes, fills the metering syringes 38, 40 with diluent (water) and returns the pipettes to the wash station 28 (FIG. 14—sensor 208), where the pipettes 30, 32 are lowered and the metering syringes are emptied for flushing the pipettes and cleaning their outer surfaces as indicated in FIG. 14. The system is concurrently preparing to begin the next sample and reagent transfer sequence by indexing the tables 64, 80 and 98 to the next desired positions.

Figure 18:
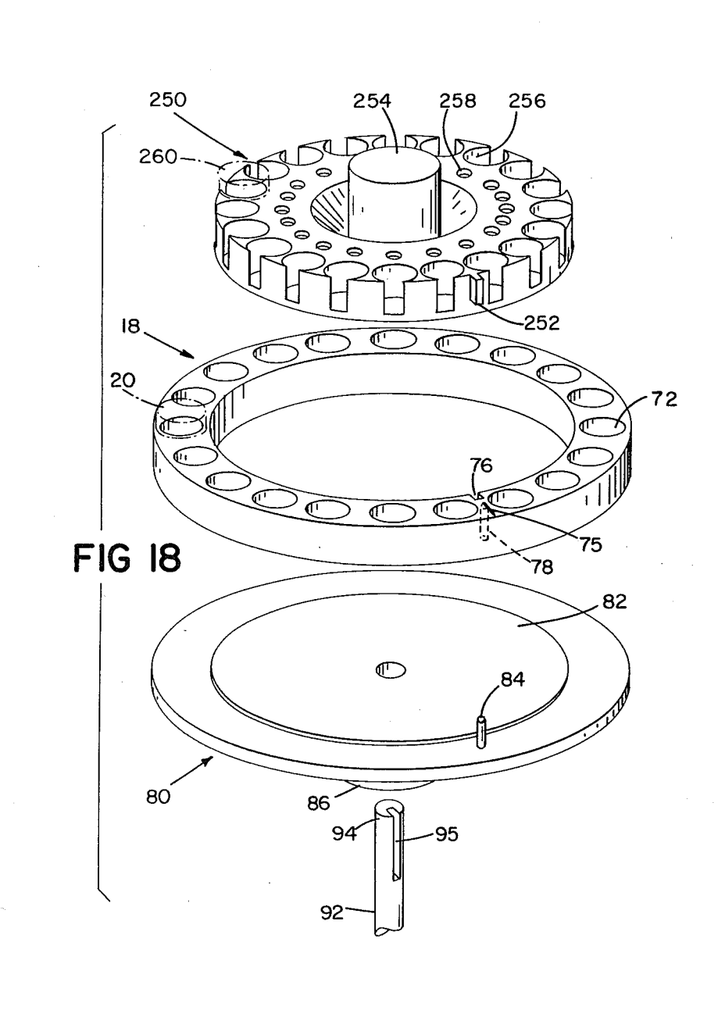
FIG. 18 is an exploded perspective view of an apparatus used for dilution in the liquid handling system of FIG. 1.
Figure 19:
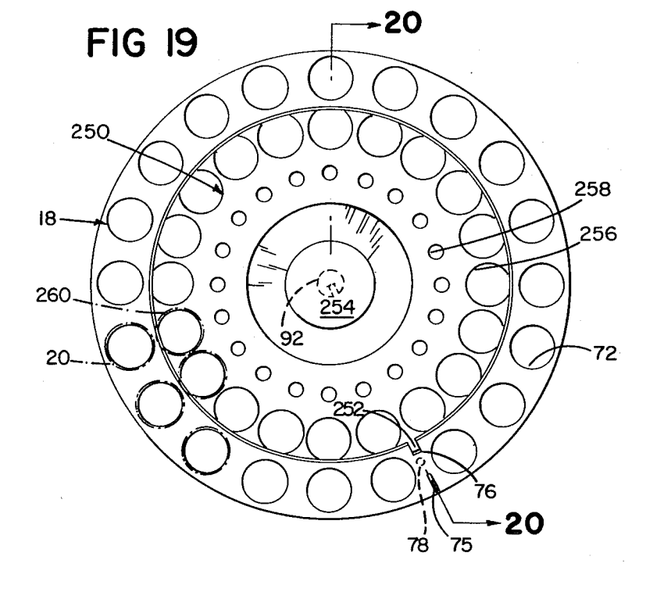
FIG. 19 is a top plan view of dilution apparatus shown in FIG. 18.
Figure 20:
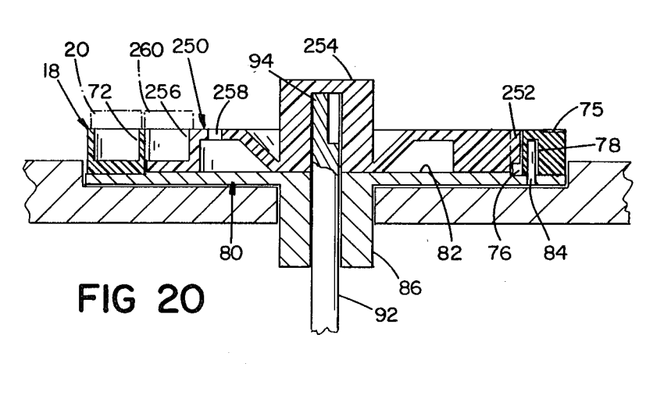
FIG. 20 is a sectional view taken along the line 20—20 of FIG. 19.

The system also provides controlled sample dilution capability. For such sample dilution operation, reagent boat table 24 is removed and sample cup table 250 (FIG. 18) is substituted. Table 250 has a projecting key 252 which engages slot 76 in sample ring 18 so that table 250 is driven and indexed with ring 18 as indicated in FIGS. 19 and 20. Table 250 has a diameter of about eleven centimeters and a height of about one centimeter with central handling knob 254 that has a diameter of about 2½ centimeters and a height of about 2½ centimeters and is piloted on but not driven by shaft 92 as hub 254 does not include a key. Table 250 has an array of twenty socket receptacles 256 for receiving ¼ milliliter sample cups 260 of the same type as carried by ring 18. Openings 258 located radially inward of socket receptacles 256 provide pipette tip clearance. Radial reinforcing webs extend from hub 254 to the annular structure in which ports 258 are formed.

Figure 21:
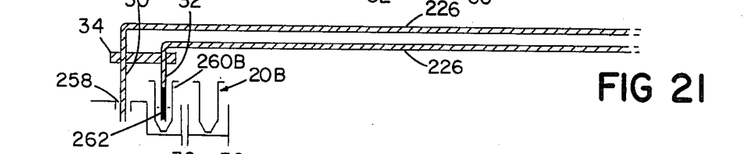
FIGS. 21 and 22 are diagrammatic views similar to FIGS. 14–17 showing the dilution operation.
Figure 22:
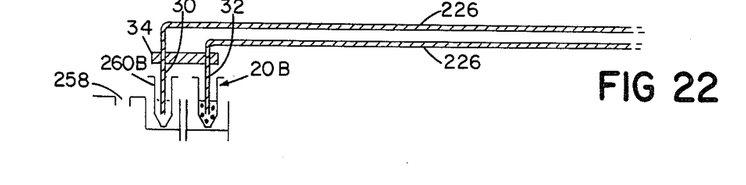

A dilution sequence is illustrated in FIG. 21 and 22. Initially (after washing), transport arm 34 is moved to the reagent position (sensor 210) and the pipettes 30, 32 are lowered as indicated in FIG. 21 and pipette 32 inserted in the sample cup 260B and pipette 30 extending through the aligned port 258. A specified volume 262 of sample (for example, four microliters) is drawn into probe 32; the probe arm 34 is raised and moved to the sample position (sensor 209) and the pipettes are lowered into the sample and dilution cups 260B and 20B respectively as indicated in FIG. 22 (the cups 20 in the outer ring being used to hold the diluted sample). In this position, metering pump 40 is operated to dispense eighty microliters into cup 20 (four microliters of sample and seventy-six microliters of diluent). The probe arm 34 is then lifted, ten microliters of air is drawn at the tip of pipette 32 by pump 40, the pipettes are again lowered, pump 40 draws eighty microliters from cup 20 and then dispenses that volume for further mixing of the diluted sample 226 in cup 20. The pipette arm 34 is then raised and moved to the wash station 28 (FIG. 14—sensor 208) for washing; and motor 88 indexes both ring 18 and sample table 250 as a unit; the transport arm 34 moves back to the reagent position (sensor 210) and the pipette transport arm 34 moves down to the position indicated in FIG. 21 to draw a specified quantity of sample from the next sample cup 260 and repeat the above described dilution sequence as programmed.

After the series of dilution sequences have been completed, the auxiliary sample cup tray 250 is replaced with the reagent tray 26 for transfer of diluted sample and reagents to the cuvettes 50 as above described.

The described transfer system will load a twenty-cuvette rotor 14, starting at a designated reference cuvette position and sequentially loading up to twenty cuvettes with sample and a single reagent in three minutes. The loading time for twenty cuvettes with sample and two reagents is four minutes. Sample volumes from two to ninety-nine microliters and reagent volumes from five to two-hundred fifty microliters may be selected with the minimum total dispensed volume for a particular test being one-hundred fifty microliters.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. Apparatus for transferring precise quantities of liquids to analysis cuvettes comprising:

a cuvette loading station for receiving an analysis cuvette;

transfer structure having two liquid handling probes fixedly mounted thereon in fixed spaced apart relation permitting simultaneous insertion of said two probes into an analysis cuvette at said cuvette loading station;

first and second storage chamber structures, each said storage chamber structure being connected to a corresponding one of said probes; first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, a plurality of sample containers on said sample container support mechanism, and sample container drive mechanism constructed and arranged for indexing said sample container support mechanism through said sample station to sequentially position successive sample containers carried by said sample container support mechanism at said sample station;

an auxiliary transporting means including an auxiliary container support mechanism, a portion of said auxiliary transporting means forming an auxiliary station, a plurality of auxiliary containers on said auxiliary container support mechanism, each said auxiliary container having a reagent storage compartment and a dry well that is open at its bottom, structure defining first and second spaced apart ports through which said two probes may be concurrently inserted, said first port providing communication with said reagent storage compartment and said second port providing communication with said dry well, and an auxiliary container drive mechanism constructed and arranged to index said auxiliary container support mechanism to selectively position said auxiliary containers carried by said auxiliary container support mechanism at said auxiliary station, wherein said cuvette loading station, said sample station and said auxiliary station are disposed on a straight line path and said transfer structure is constructed and arranged to move said two probes along said straight path with tips of said two probes defining a line parallel with said straight line path, and wherein said first port and said dry well of that one of said auxiliary containers which is positioned at said auxiliary station is disposed on said straight line path, the spacing of said sample and auxiliary stations corresponding to the fixed spacing of said two probes so that said two probes may be simultaneously inserted into those of said sample and auxiliary containers which are located at said sample and auxiliary stations, respectively;

a first drive mechanism constructed and arranged for moving said transfer structure along said straight line path between said cuvette loading, sample, and auxiliary stations;

a second drive mechanism operative at said loading, sample, and auxiliary stations for selectively inserting the tips of said two liquid handling probes into a cuvette in said cuvette loading station, that one of said auxiliary containers which is located in said auxiliary station, and concurrently into both one of said sample containers located at said sample station and one of said auxiliary containers located at said auxiliary station; and control means for operating said first and second drive mechanisms and said liquid metering means to transfer liquid from sample and auxiliary containers at said sample and auxiliary stations to an analysis cuvette at said cuvette loading station.

2. The apparatus of claim 1 wherein said apparatus further includes a plurality of analysis cuvettes, and cuvette transporting means for indexing said plurality of analysis cuvettes through said cuvette loading station, each said analysis cuvette having two compartments with corresponding spaced loading ports, the spacing between said probes corresponding to the spacing of said loading ports of said analysis cuvette compartments.

3. The apparatus of claim 2 wherein said cuvette transporting means includes a centrifugal analyzer rotor having a plurality of analysis cuvettes arranged in annular array thereon, and wherein said cuvette transporting means further includes means for rotating said rotor for sequentially positioning successive ones of said analysis cuvettes at said cuvette loading station.

4. The apparatus of claim 3 wherein said sample container support mechanism includes structure that defines an annular array of sample container receiving elements, and said sample container drive mechanism is positioned and arranged to rotate said annular array of sample container receiving elements for sequentially positioning successive sample containers at said sample stations.

5. The apparatus of claim 4 wherein said support mechanisms for sample and auxiliary containers are constructed and arranged to position said sample and auxiliary containers in coaxial annular arrays.

6. The apparatus of claim 5 wherein said auxiliary container support mechanism includes an annular array of coupling elements constructed and arranged for securing auxiliary containers on said auxiliary container support mechanism.

7. The apparatus of claim 6 wherein each of said auxiliary containers includes a female coupling structure formed therein and said annular array of coupling elements includes a series of male coupling portions constructed and arranged for releasably engaging said female coupling structures of said auxiliary containers.

8. The apparatus of claim 5 wherein said auxiliary container drive mechanism includes means for coupling said auxiliary container support mechanism to said sample container drive mechanism so that successive sample and auxiliary containers may be coordinately positioned at said sample and auxiliary stations respectively.

9. The apparatus of claim 5 wherein said auxiliary container drive mechanism includes means for rotating said auxiliary container support mechanism independently of said sample container drive mechanism so that sample and auxiliary containers may be selectively and independently positioned at said sample and auxiliary stations respectively.

10. The apparatus of claim 1 wherein said transfer structure includes cantilever arm structure with said two probes secured at one end thereof.

11. The apparatus of claim 1 and further including a diluent supply, and a valve arrangement for selectively connecting each of said metering means to said diluent supply and to its corresponding storage chamber, each said metering means, when connected to its storage chamber, controlling flow of liquid into and out of said storage chamber through its said probe.

12. The apparatus of claim 11 wherein said cuvette transporting means includes a centrifugal analyzer rotor having a plurality of analysis cuvettes arranged in annular array thereon, and wherein each said analysis cuvette has two compartments with corresponding spaced loading ports, the spacing between said probes corresponding to the spacing of said loading ports of said analysis cuvette compartments, and said cuvette transporting means further including means for indexing the said analysis cuvettes of said rotor past said loading station for sequentially positioning successive ones of said analysis cuvettes at said cuvette loading station.

13. Apparatus for transferring precise quantities of liquids to analysis cuvettes comprising:

a cuvette loading station for receiving an analysis cuvette;

transfer structure having two liquid handling probes fixedly mounted thereon in fixed spaced apart relation permitting simultaneous insertion of said two probes into an analysis cuvette at said cuvette loading station;

first and second storage chamber structures, each said storage chamber structure being connected to a corresponding one of said probes;

first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, a plurality of sample containers on said sample container support mechanism, and sample container drive mechanism constructed and arranged for indexing said sample container support mechanism through said sample station to sequentially position successive sample containers carried by said sample container support mechanism at said sample station;

an auxiliary transporting means including an auxiliary container support mechanism, a portion of said auxiliary transporting means forming an auxiliary station, a plurality of auxiliary containers on said auxiliary container support mechanism, said auxiliary container support mechanism including an annular array of coupling elements constructed and arranged for releasably securing auxiliary containers on said auxiliary container support mechanism, each said auxiliary container having a reagent storage compartment and a dry well that is open at its bottom, and being of sector shaped configuration with a generally vertical curved outer wall, generally vertical side walls that are disposed at an angle to one another and joining at a side opposite said outer wall, said top wall being generally horizontal, and said bottom wall being generally horizontal, a portion of said bottom wall defining a well, structure in said top wall defining first and second spaced apart ports through which said two probes may be concurrently inserted, said first port providing communication with said reagent storage compartment and said second port providing communication with said dry well, and an auxiliary container drive mechanism constructed and arranged to index said auxiliary container support mechanism to selectively position said auxiliary containers carried by said auxiliary container support mechanism at said auxiliary station, wherein said curvette loading station, said sample station and said auxiliary station are disposed on a straight line path and said transfer structure is constructed and arranged to move said two probes along said straight path with tips of said two probes defining a line parallel with said straight line path, and wherein said first port and said dry well of that one of said auxiliary containers which is positioned at said auxiliary station is disposed on said straight line path, the spacing of said sample and auxiliary stations corresponding to the fixed spacing of said two probes so that said two probes may be simultaneously inserted into those of said sample and auxiliary containers which are located at said sample and auxiliary stations, respectively;

said auxiliary container drive mechanism including means for rotating said auxiliary container support mechanism independently of said sample container drive mechanism so that sample and auxiliary containers may be selectively and independently positioned at said sample and auxiliary stations respectively, a first drive mechanism constructed and arranged for moving said transfer structure along said straight line path between said cuvette loading, sample, and auxiliary stations;

a second drive mechanism operative at said loading, sample, and auxiliary stations for selectively inserting the tips of said two liquid handling probes into a cuvette in said cuvette loading station, that one of said auxiliary containers which is located in said auxiliary station, and concurrently into both one of said sample containers located at said sample station and one of said auxiliary containers located at said auxiliary station; and control means for operating said first and second drive mechanisms and said liquid metering means to transfer liquid from sample and auxiliary containers at said sample and auxiliary stations to an analysis cuvette at said cuvette loading station.

14. Apparatus for transferring precise quantities of liquids to analysis cuvettes comprising:

a cuvette loading station for receiving an analysis cuvette;

transfer structure having a pivotally mounted cantilever arm structure with two liquid handling probes fixedly mounted at one end thereon in fixed spaced apart relation permitting simultaneous insertion of said two probes into an analysis cuvette at said cuvette loading station;

first and second storage chamber structures, each said storage chamber structure being connected to a corresponding one of said probes; first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, and sample container drive mechanism constructed and arranged for indexing said sample container support mechanism through said sample station to sequentially position successive sample containers carried by said sample container support mechanism at said sample station;

an auxiliary transporting means including an auxiliary container support mechanism constructed and arranged for supporting a plurality of auxiliary containers, a portion of said auxiliary transporting means forming an auxiliary station, and an auxiliary container drive mechanism constructed and arranged to index said auxiliary container support mechanism to selectively position auxiliary containers carried by said auxiliary container support mechanism at said auxiliary station, the spacing of said sample and auxiliary stations permitting said two probes to be simultaneously inserted into sample and auxiliary containers at said sample and auxiliary stations respectively;

a first drive mechanism constructed and arranged for moving said cantilever arm structure along said straight line path between said cuvette loading, auxiliary, and sample stations, said first drive mechanism including a lead screw disposed parallel to said straight line path;

a second drive mechanism including cam means rotatable about an axis parallel to said lead screw for pivoting said cantilever arm structure to move the tips of said liquid handling probes in a direction generally perpendicular to said straight line translational movement of said cantilever arm structure to concurrently insert the tips of said two liquid handling probes into a cuvette in said cuvette loading station, an auxiliary container in said auxiliary station, and concurrently into a sample container at said sample station and an auxiliary container at said auxiliary station; and control means for operating said first and second drive mechanisms and said liquid metering means to transfer liquid from sample and auxiliary containers at said sample and auxiliary stations to an analysis cuvette at said cuvette loading station.

15. The apparatus of claim 14 wherein said cantilever arm structure includes two members that are hinged together, limit means for positioning said members in aligned relation, and releasable latch structure for holding said members in aligned position.

16. Apparatus for transferring precise quantities of liquids to analysis cuvettes comprising:

a cuvette loading station for receiving an analysis cuvette;

transfer structure having cantilever arm structure with two liquid handling probes fixedly mounted at one end thereof in fixed spaced apart relation;

first and second storage chamber structures, each said storage chamber structure being connected to a corresponding one of said probes;

first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, and sample container drive mechanism constructed and arranged for indexing said sample container support mechanism through said sample station to sequentially position successive sample containers carried by said sample container support mechanism at said sample station;

an auxiliary transporting means including, an auxiliary container support mechanism for supporting a plurality of auxiliary containers, a portion of said auxiliary transporting means forming an auxiliary station, and an auxiliary container drive mechanism for moving said auxiliary container support mechanism to selectively position auxiliary containers carried by said auxiliary container support mechanism at said auxiliary station;

a first drive mechanism constructed and arranged for providing translational movement between said cantilever arm structure and said cuvette loading, auxiliary, and sample stations, a second drive mechanism operative at said loading, auxiliary and sample stations constructed and arranged for selectively moving tips of said liquid handling probes in a direction generally perpendicular to said translational movement of said cantilever arm structure to concurrently insert the tips of said two liquid handling probes into and withdraw said probes from containers;

said cantilever arm structure including a releasable latch structure constructed and arranged to disconnect said cantilever arm structure from said second drive mechanism in response to a force in the range between three and twelve ounces resisting the insertion movement of said probes; and control means for operating said first and second drive mechanisms and said liquid metering means to transfer liquid materials from sample and auxiliary containers at said sample and auxiliary stations to an analysis cuvette at said cuvette loading station.

17. Apparatus for transferring precise quantities of liquids to analysis cuvettes comprising:

a cuvette loading station for receiving an analysis cuvette;

transfer structure having cantilever arm structure with two liquid handling probes fixedly mounted at one end thereof in fixed spaced apart relation, said cantilever arm structure including two members that are hinged together, one of said members forming an arm member and having said two probes fixedly mounted thereon, limit means for positioning said members in aligned relation, and releasable latch structure for holding said members in aligned position, said releasable latch structure including resilient means arranged to release said latch and allow the arm member carrying said probes to pivot upwardly in response to a force in the range between three and twelve ounces resisting the downward movement of said probes, first and second storage chamber structures, each said storage chamber structure being connected to a corresponding one of said probes; first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, and sample container drive mechanism constructed and arranged for indexing said sample container support mechanism through said sample station to sequentially position successive sample containers carried by said sample container support mechanism at said sample station;

an auxiliary transporting means including an auxiliary container support mechanism for supporting a plurality of auxiliary containers, a portion of said auxiliary transporting means forming an auxiliary station, and an auxiliary container drive mechanism for moving said auxiliary container support mechanism to selectively position auxiliary containers carried by said auxiliary container support mechanism at said auxiliary station, the spacing of said sample and auxiliary stations permitting said two probes to be simultaneously inserted into sample and auxiliary containers at said sample and auxiliary stations, respectively;

a first drive mechanism constructed and arranged for providing translational movement between said cantilever arm structure and said cuvette loading, auxiliary, and sample stations, a second drive mechanism operative at said cuvette loading, auxiliary and sample stations and constructed and arranged for selectively moving the tips of said liquid handling probes in a direction generally perpendicular to said translational movement of said cantilever arm structure to concurrently insert the tips of said two liquid handling probes into and withdraw said probes from containers; and control means for operating said first and second drive mechanisms and said liquid metering means to transfer liquid from sample and auxiliary containers at said sample and auxiliary stations to an analysis cuvette at said cuvette loading station.

18. Apparatus for transferring precise quantities of liquids to analysis cuvettes comprising:

a cuvette loading station for receiving an analysis cuvette;

transfer structure having cantilever arm structure with two liquid handling probes fixedly mounted at one end therof in fixed spaced apart relation;

first and second storage chamber structures, each said storage chamber structure being connected to a corresponding one of said probes; first and second liquid metering means, each said metering means being connected to a corresponding one of said first and second storage chamber structures and being constructed and arranged to control flow of liquid into and out of its respective storage chamber through its respective probe;

a sample transporting means including a sample container support mechanism, a portion of said sample transporting means forming a sample station, and sample container drive mechanism for moving said sample container support mechanism past said sample station to sequentially position successive sample containers at said sample station;

an auxiliary transporting means including an auxiliary container support mechanism for supporting a plurality of auxiliary containers, a portion of said auxiliary transporting means forming an auxiliary station, and an auxiliary container drive mechanism for moving said auxiliary container support mechanism to selectively position auxiliary containers carried by said auxiliary container support mechanism at said auxiliary station;

a wash station having two wells spaced to receive the two probes carried by said transfer structure, each said well having a width dimension slightly larger than the outside dimension of the probes so that, for each of said wells, liquid discharged from a respective one of said probes while a respective one of said probes is received in said well flows upwardly along an outer surface of said probe in cleaning action, a peripheral wall upstanding from and extending around the tops of said two wells to define a containment chamber, and a drain port in the base of said containment chamber for transferring excess liquid to waste;

a first drive mechanism constructed and arranged for providing translational movement between said cantilever arm structure and said cuvette loading, auxiliary, and sample stations, a second drive mechanism operative at said cuvette loading, wash, auxiliary and sample stations for selectively moving the tips of said liquid handling probes in a direction generally perpendicular to said translational movement of said cantilever arm structure to concurrently insert the tips of said two liquid handling probes into and withdraw said probes from containers, said cantilever arm structure including releasable latch structure arranged to disconnect said cantilever arm structure from said second drive in response to a force in the range between three and twelve ounces resisting the insertion movement of said probes, and control means for operating said first and second drive mechanisms and said liquid metering means to transfer liqued materials from sample and auxiliary containers at said sample and auxiliary stations to an analysis cuvette at said cuvette loading station.

* * * * *

UNITED STATES PATENT AND TRADEMARK OFFICE
CERTIFICATE OF CORRECTION

PATENT NO. : 4,761,268

DATED : August 2, 1988

INVENTOR(S) : Marlo R. Anderson, et al.

It is certified that error appears in the above-identified patent and that said Letters Patent are hereby corrected as shown below:

The following references cited in the Information Disclosure Statement were omitted from the patent:

| U.S. Patent No. | Date | Name |
|---|---|---|
| 4,298,571 | 11/3/81 | DiFulvio, et al. |
| 4,313,735 | 1/19/82 | Yamashita, et al. |
| 4,341,736 | 7/27/82 | Drbal, et al. |
| 4,360,360 | 11/23/82 | Chiknas |
| 4,373,812 | 2/15/83 | Stein, et al. |

Col. 7, line 56, change "strighht" to --straight--.

Col. 8, line 31, change "tubs" to --tubes--.

Col. 9, line 64, change "and" to --with--.

Signed and Sealed this

Eleventh Day of April, 1989

*Attest:*

DONALD J. QUIGG

*Attesting Officer*  *Commissioner of Patents and Trademarks*